United States Patent
Park

(10) Patent No.: US 11,225,440 B2
(45) Date of Patent: Jan. 18, 2022

(54) METHOD FOR MANUFACTURING ZIRCONIA BLOCK FOR DENTAL PROSTHESIS HAVING LAYERED COLOR GRADIENT BY WATER ABSORPTION RATE

(71) Applicant: Tae Seok Park, Seoul (KR)

(72) Inventor: Tae Seok Park, Seoul (KR)

( * ) Notice: Subject to any disclaimer, the term of this patent is extended or adjusted under 35 U.S.C. 154(b) by 91 days.

(21) Appl. No.: 16/618,174

(22) PCT Filed: Mar. 7, 2018

(86) PCT No.: PCT/KR2018/002691
§ 371 (c)(1),
(2) Date: Nov. 29, 2019

(87) PCT Pub. No.: WO2018/225934
PCT Pub. Date: Dec. 13, 2018

(65) Prior Publication Data
US 2021/0155551 A1    May 27, 2021

(30) Foreign Application Priority Data
Jun. 7, 2017 (KR) .................... 10-2017-0070556

(51) Int. Cl.
*C04B 35/48* (2006.01)
*C04B 35/626* (2006.01)
(Continued)

(52) U.S. Cl.
CPC ...... *C04B 35/6261* (2013.01); *A61C 13/0835* (2013.01); *C04B 35/48* (2013.01);
(Continued)

(58) Field of Classification Search
CPC ................ C04B 35/6261; C04B 35/48; C04B 35/62685; C04B 41/0072; C04B 41/4535;
(Continued)

(56) References Cited

U.S. PATENT DOCUMENTS

2007/0292597 A1* 12/2007 Ritzberger ............. A61K 6/813
427/2.29
2008/0306168 A1    12/2008 Craig et al.
2018/0072628 A1*  3/2018 Cornell ............. A61C 13/0022

FOREIGN PATENT DOCUMENTS

KR    101276816 B1    6/2008
KR    101142805 B1    5/2012
(Continued)

OTHER PUBLICATIONS

International Search Report of PCT/KR2018/002691, dated Jun. 14, 2018, English translation.

*Primary Examiner* — Karl E Group
*Assistant Examiner* — Cameron K Miller
(74) *Attorney, Agent, or Firm* — SLIP Law Group, LLC

(57) ABSTRACT

The present invention relates to a method for manufacturing a zirconia block for a dental prosthesis having a layered color gradient by a water absorption rate, in which the permeation degree of a coloring solution is controlled by setting a different particle size of powder for each layer of the zirconia block on the basis of the property that the amount of water absorption per hour is differentiated according to the particle size of powder, and as a result, the zirconia block is constituted so as to realize an esthetically excellent resultant product with the same color as natural teeth without carrying out the existing coloring liquid process for zirconia.

7 Claims, 2 Drawing Sheets

(51) Int. Cl.
*A61C 13/083* (2006.01)
*C04B 41/00* (2006.01)
*C04B 41/45* (2006.01)
*C04B 111/00* (2006.01)

(52) U.S. Cl.
CPC .... *C04B 35/62685* (2013.01); *C04B 41/0072* (2013.01); *C04B 41/4535* (2013.01); *C04B 2111/00836* (2013.01); *C04B 2235/3212* (2013.01); *C04B 2235/3225* (2013.01); *C04B 2235/3418* (2013.01); *C04B 2235/422* (2013.01); *C04B 2235/5436* (2013.01); *C04B 2235/5445* (2013.01); *C04B 2235/9661* (2013.01)

(58) Field of Classification Search
CPC ............. C04B 2111/00836; C04B 2235/3212; C04B 2235/3225; C04B 2235/3418; C04B 2235/422; C04B 2235/5436; C04B 2235/5445; C04B 2235/9661; A61C 13/0835
See application file for complete search history.

(56) References Cited

FOREIGN PATENT DOCUMENTS

| | | | |
|---|---|---|---|
| KR | 101276616 | B1 | 6/2013 |
| KR | 101324467 | B1 | 11/2013 |
| KR | 101601948 | B1 | 3/2016 |
| KR | 1020170023436 | A | 3/2017 |
| KR | 101792680 | B1 | 11/2017 |

\* cited by examiner

METHOD FOR MANUFACTURING ZIRCONIA BLOCK FOR DENTAL PROSTHESIS HAVING LAYERED COLOR GRADIENT BY WATER ABSORPTION RATE

CROSS-REFERENCE TO RELATED APPLICATIONS

This application is the U.S. National Phase under 35 U.S.C. § 371 of International Application No. PCT/KR2018/002691 filed on Mar. 7, 2018, which in turn claims the benefit of Korean Application No. 10-2017-0070556, filed on Jun. 7, 2017, the disclosures of which are incorporated by reference into the present application.

TECHNICAL FIELD

The present invention relates to a method for manufacturing a zirconia block for a dental prosthesis with improved aesthetic properties, and more particularly, to a method for manufacturing a zirconia block for a dental prosthesis having a layered color gradient by a water absorption rate, in which the permeation degree of a coloring solution is controlled by setting a different particle size of powder for each layer of the zirconia block on the basis of the property, that the amount of water absorption per hour is differentiated according to the particle size of powder, and as a result, the zirconia block is constituted so as to realize an esthetically excellent resultant product with the same color as natural teeth without carrying out the existing coloring liquid process for zirconia.

BACKGROUND ART

Recently, a material for a dental prosthesis has been replaced with zirconia which is excellent in biocompatibility, similar to natural teeth in appearance, excellent in aesthetic properties, and improved in durability due to high mechanical properties.

Meanwhile, the most important thing when a dental prosthesis is manufactured using zirconia is to improve aesthetic properties by applying a color gradient to zirconia, such that the dental prosthesis has a color corresponding to that of natural teeth. In the related art, a color gradient is applied on the basis of the color guide, and a work process called a coloring liquid for zirconia is further included in order to induce a more natural color gradient. Here, the coloring liquid for zirconia refers to a method of applying a different color to each part of a zirconia block.

As an example of the existing methods, Korean Patent No. 10-4142805 "Method for manufacturing color zirconia block endowed with aesthetic properties" is described.

In the related art, there is a method in which each site of a zirconia block is immersed in a large number of coloring solutions prepared for inducing the color gradient of teeth from light color to dark color, and then the coloring solution is implanted by applying heat thereto, and as another method, zirconia powder is introduced into each coloring solution having a different color, and then the coloring solution is permeated into the powder by applying heat thereto, the powder permeated with the coloring solution is brought out of the coloring solution and dried, and then a zirconia block having a color gradient is produced by injecting the powder into a pressurization device to pressurize the powder on the basis of the color guide.

Here, the disadvantage of the related art is that all the parts of the zirconia block are all composed at the same water absorption rate, so that it is inconvenient for an operator to color each part while replacing the coloring solution.

In order to eliminate the inconvenience of the coloring liquid working process for zirconia, Korean Patent No. 10-1276816 "Method for manufacturing zirconia block for artificial teeth having color gradient" has been proposed.

The related art is a method for producing a zirconia block having a color gradient by, separately preparing a colored zirconia powder and a white zirconia powder to mix the powders, blending the white zirconia powder with the colored zirconia powder at different weight ratios to prepare a plurality of raw materials showing different colors, injecting the raw material into a mold for compression molding in order of light color to dark color or dark color to light color, and then pressurizing the raw material.

However, since the method in the related art requires an advanced technology in which the colored zirconia powder and the white zirconia powder need to be prepared at different weight ratios, the aforementioned method incurs a problem in that the productivity is remarkably reduced by personnel costs, production costs, and the like.

Therefore, there is an urgent need for a method for manufacturing a zirconia block, in which the zirconia block may be prepared readily and rapidly and have a constant color gradient by applying a color gradient corresponding to that of natural teeth to a zirconia block, and improving an existing coloring liquid method for zirconia which is complicated and inconvenient and a method for mixing colored and white zirconia powders.

DISCLOSURE

Technical Problem

The present invention has been created to more positively solve problems of an existing coloring liquid method in which the production unit costs have been increased because the quality of the color gradient is not consistent depending on the operator's ability and a special technology is required, and a problem to be solved is to readily and conveniently provide a zirconia block in which the color gradient may be consistently expressed by providing a zirconia block having a differentiated water absorption rate for each layer.

Technical Solution

In order to solve the aforementioned problem, a method for manufacturing a zirconia block for a dental prosthesis having a layered color gradient by a water absorption rate proposed by the present invention is as follows.

A method for manufacturing a zirconia block for a dental prosthesis having a layered color gradient by a water absorption rate may include: 1) a main raw material separation step of preparing a main raw material by pulverizing zirconia to different particle sizes and dividing the zirconia at each particle size; 2) a sub raw material mixing step of introducing and mixing a sub raw material whose water absorption rate is controlled at each main raw material having a different particle size; 3) a raw material pressurization step of injecting the main raw material mixed with the sub raw material into a mold for compression molding in an order of particle size, and then compression molding the main raw material in the form of a block; 4) a raw material implantation step of inducing a coloring solution to permeate into the zirconia block by putting the zirconia block molded in step 3) into a tank containing the coloring solution and then applying heat to the tank; and 5) a heat treatment finishing step of drying the zirconia block into which the coloring solution in step 4) penetrates, and then calcining the zirconia block with heat at room temperature.

1) The main raw material separation step may pulverize the zirconia into a particle size each differentiated within a range of 30 nm to 10 μm.

2) The sub raw material mixing step may further include: 2-1) a sub raw material preparation step of preparing the sub raw material by pulverizing the sub raw material into a particle size each differentiated within a range of 30 nm to 10 μm and dividing the sub raw material at each particle size; and 2-2) a sub raw material introduction step of each introducing the sub raw material prepared at each particle size into each of the main raw materials having the same particle size.

3) The raw material pressurization step may include: 3-1) a step of firstly pressurizing the raw material at 500 to 600 kg/km$^2$; 3-2) a step of secondly pressurizing the raw material at 700 to 800 kg/km$^2$; and 3-3) a step of thirdly pressurizing the raw material at 800 to 1000 kg/km$^2$.

4) The raw material implantation step may include: 4-1) a step of heating a coloring solution to 50 to 100° C.; and 4-2) a step of putting a zirconia block into the heated coloring solution.

5) The heat treatment finishing step may include: 5-1) a step of firstly drying the zirconia block in a drying furnace in which hot wind at 5 to 20° C. is provided from all sides for 20 to 30 minutes; 5-2) a step of secondly drying the zirconia block in a drying furnace in which hot wind at 10 to 25° C. is provided from all sides for 10 to 20 minutes; and 5-3) a step of putting the dried zirconia block into a sintering furnace and calcining the zirconia block.

The sub raw material may be selected from the group consisting of a silica powder, a hydroxyapatite powder, an yttrium oxide powder, a carbon powder, and a mixture thereof.

Advantageous Effects

According to the present invention composed of the constitution as described above, as a zirconia block is divided at each layer and the water absorption rate is provided differently at each divided layer, there is an effect capable of producing a high-quality zirconia block for a dental prosthesis in which a color gradient is exhibited constantly by inducing the degree of color sense in which the coloring solution is implanted at each layer to be different by varying the amount of solution permeated at the corresponding layer.

Further, the sub raw material has another effect in which as a powder selected from the group consisting of a silica powder, a hydroxyapatite powder, an yttrium oxide powder, a carbon powder, and a mixture thereof is mixed with a main raw material, the water absorption rate of the zirconia block at each layer is controlled minutely, and thus the limitation of the color range of the zirconia block is improved.

Finally, since the zirconia block is directly produced by medical equipment production companies, there is an effect in which a patient can be immediately treated with a consistently high-quality crown for an implant having a color gradient without a separate coloring liquid work in a dental clinic or a dental laboratory.

EXPLANATION OF REFERENCE NUMERALS AND SYMBOLS

Figure 1:
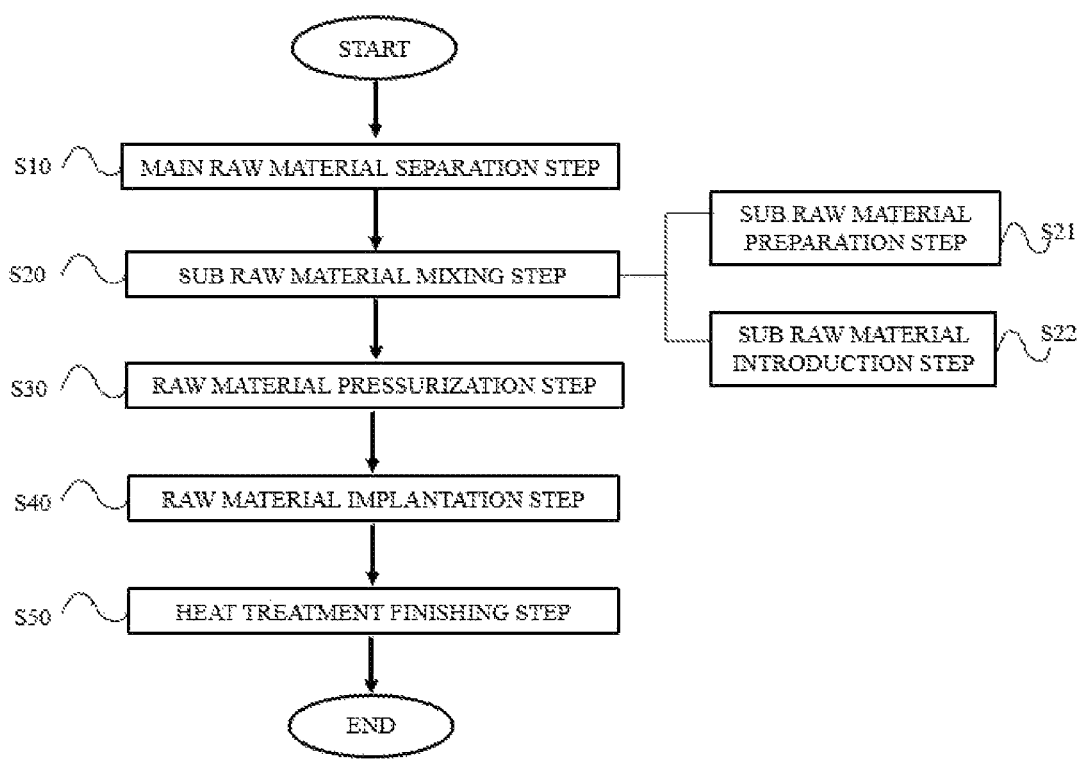
FIG. 1 is a flow-chart of enumerating a method for manufacturing a zirconia block for a dental prosthesis having a layered color gradient by a water absorption rate according to preferred exemplary embodiments of the present invention in sequence.

S10 Main raw material separation step
S20 Sub raw material mixing step
S30 Raw material pressurization step
S40 Raw material implantation step
S50 Heat treatment finishing step

BEST MODE

Before the present invention is described, the meaning of the terms used in the present invention will be described.

The present invention relates to a method for manufacturing a zirconia block for a dental prosthesis having a layered color gradient by a water absorption rate, the method including: 1) a main raw material separation step of preparing a main raw material by pulverizing zirconia at different particle sizes and dividing the zirconia at each particle size; 2) a sub raw material mixing step of introducing and mixing a sub raw material whose water absorption rate is controlled at each main raw material having a different particle size; 3) a raw material pressurization step of injecting the main raw material mixed with the sub raw material into a mold for compression molding in an order of particle size, and then compression molding the main raw material in the form of a block; 4) a raw material implantation step of inducing a coloring solution to permeate into the zirconia block by putting the zirconia block molded in step 3) into a tank containing the coloring solution and then applying heat to the tank; and 5) a heat treatment finishing step of drying the zirconia block into which the coloring solution in step 4) penetrates, and then calcining the zirconia block with heat at room temperature.

Hereinafter, the configuration of the present invention and the operations and effects thereof will be described collectively with reference to the accompanying drawings.

The benefits and features of the present invention, and the methods of achieving the benefits and features will become apparent with reference to examples to be described below in detail along with the accompanying drawings. However, the present invention is not limited to the examples to be disclosed below, but may be implemented in various other forms, and the present examples are only provided for rendering the disclosure of the present invention complete and for fully representing the scope of the invention to a person with ordinary skill in the technical field to which the present invention pertains, and the present invention will be defined only by the scope of the claims. And throughout the specification, like reference numerals refer to like constituent elements.

The present invention relates to a method for manufacturing a zirconia block for a dental prosthesis with improved aesthetic properties.

First of all, it should be well known that the present invention relates to a method for manufacturing a zirconia block for a dental prosthesis having a layered color gradient by a water absorption rate, in which the permeation degree of a coloring solution is controlled by setting a different particle size of powder for each layer of the zirconia block on the basis of the property, that the amount of water absorption per hour is differentiated according to the particle size of powder, and as a result, the zirconia block is constituted so as to realize an esthetically excellent resultant product with the same color as natural teeth without carrying out the existing coloring liquid process for zirconia.

Further, the coloring solution of the present invention is a solution obtained by dissolving iron (II) chloride ($FeCl_{3.6}H_2O$), molybdenum chloride ($MoCl3$), chromic chloride hydrate ($CrCl_{3.6}H_2O$), vanadium trichloride ($VCl_3$), and the like, and is on the basis of a method for coloring a zirconia block by immersing the zirconia block into the foregoing coloring solution.

As in the flow-chart enumerated in FIG. 1, the present invention produces a zirconia block for a dental prosthesis in which a color gradient is formed by a water absorption rate by sequentially performing: a main raw material separation step (S10); a sub raw material mixing step (S20); a raw material pressurization step (S30); a raw material implantation step (S40); and a heat treatment finishing step (S50).

The main raw material separation step (S10) refers to a step of preparing a main raw material by pulverizing zirconia at different particle sizes and dividing the zirconia at each particle size. For example, there is a difference in ability to absorb water in proportion to the size of the powder particles, and the finer the size of the particles becomes, the more the ability, to absorb water is improved. The reason is that the smaller the particles of the powder are, the higher the number of separation spaces between powders is, and the smaller the area of the space is, such that according to the Bernoulli's principle in which water moves from a wider space to a narrower space, a larger amount of water can be absorbed than in a zirconia block composed of a powder having a large particle size.

As described above, the present invention prepares a main raw material by pulverizing the main raw material, that is, zirconia at different particle sizes and dividing the pulverized main raw material at each particle size in order to apply color gradient to the zirconia using the Bernoulli's principle in which the water absorption rate varies depending on the particle size. More specifically, it corresponds to the most preferred example to pulverize zirconia at each different particle size within a range of 30 nm to 10 μm.

The ground in which the particle size of the zirconia powder corresponds to a preferred example is on the basis of a result by repeated experiments as follows.

Figure 2:
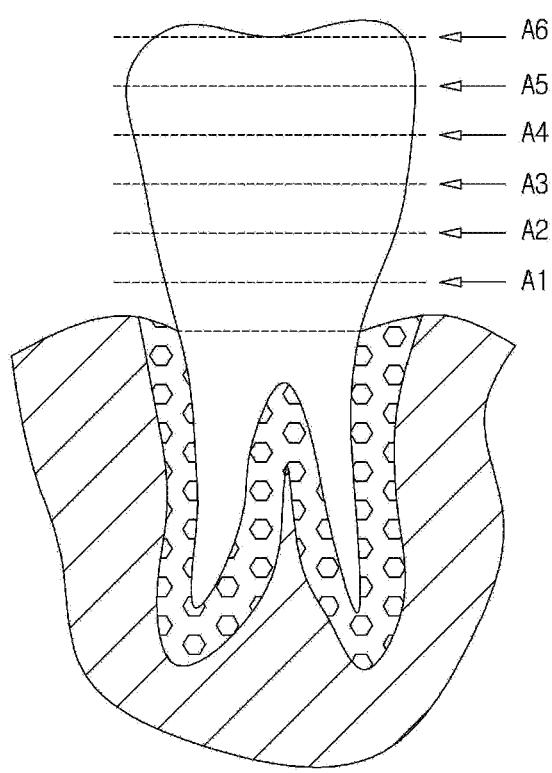
FIG. 2 is a view of a layered division description of a natural tooth.

Prior to the experiment, a natural tooth is divided into 6 layers in total from the dental root to the top as illustrated in FIG. 2, and a source code of the most suitable pastel-tone color table is imparted to each layer. Furthermore, 50 or so types of zirconia blocks obtained by pulverizing zirconia to a particle size of 0.03 μm to 10 μm, and then injecting 50 or so types of pulverized powders into a mold for compression molding, and pressurizing the pulverized powders were introduced into a coloring solution. The zirconia block introduced into the coloring solution created an environment under which a color rapidly permeates into the zirconia block by heating the zirconia block for about 5 to 10 minutes, and a block showing a color which was the most similar to the source code of a natural tooth was chosen among 50 or so types of zirconia blocks to which the color was implanted by the foregoing work procedure, and the particle size of the corresponding block and the accuracy of the corresponding block with the source code were recorded as the percentage.

TABLE 1

Color contrast table of natural tooth at each particle size

| Classification | Natural tooth (Source code) | Zirconia block for crown by Examples | | | | | |
|---|---|---|---|---|---|---|---|
| | | Particle size | Accuracy | Particle size | Accuracy | Particle size | Accuracy |
| A1 | #FFCBCB | 0.03 μm | 99.5% | 0.1 μm | 98% | 0.15 μm | 92% |
| A2 | #FFDDDD | 0.15 μm | 99% | 0.2 μm | 97.5% | 0.3 μm | 91.5% |
| A3 | #FFE6DC | 0.3 μm | 98.5% | 0.35 μm | 98% | 0.4 μm | 97% |
| A4 | #FFDCDC | 0.4 μm | 99.5% | 0.5 μm | 97.5% | 0.55 μm | 92.5% |
| A5 | #FFEFEF | 0.55 μm | 99% | 0.6 μm | 97.5% | 0.65 μm | 95% |
| A6 | #FFFFFF | 0.65 μm | 100% | 1.5 μm | 100% | 10 μm | 100% |

<Color Contrast Table of Natural Tooth at Each Particle Size>

As in the foregoing comparison table, it could be seen that the source code of A1 corresponding to the dental root of a natural tooth was '#FFCBCB' and was the most similar to the color of a zirconia block having a particle size of 0.03 μm to 0.15 μm, and among them, the particle size of 0.06 μm was 99.7% identical to the source code of A1, and 0.03 μm was 99.5%, 0.1 μm was 98%, 0.12 μm was 95%, and 0.15 μm was 92% in terms of accuracy, and 0.06 μm was the most accurate. Accordingly, in A1 corresponding to the dental root, it is most preferred to use a zirconia powder pulverized to a size of 0.06 μm. Further, the source code of A2 corresponding to an one step upper part from the dental root of a natural tooth was '#FFDDDD', and was the most similar to the color of a zirconia block having a particle size of 0.15 μm to 0.3 μm, and among them, the accuracy was the highest in the order of a particle size of 0.15 μm, 0.18 μm, 0.2 μm, 0.24 μm, 0.27 μm, and 0.3 μm. Accordingly, in A2, it is most preferred to use a zirconia powder pulverized to a size of 0.15 μm. In addition, A3, A4, A5, and A6 incorporated the most equal color at 0.3 μm, 0.4 μm, 0.55 μm, and 0.65 μm, respectively.

Meanwhile, the block having a particle size of 0.65 μm or more had a very, insignificant amount of absorbing the coloring solution, and thus exhibited a color sense of white without any significant differentiation from the source code of A6.

The foregoing sub raw material mixing step (S20) refers to a step of introducing and mixing a sub raw material whose water absorption rate is controlled at each main raw material. Here, as a material for the sub raw material, any one material is selected and used from a silica powder, a hydroxyapatite powder, an yttrium oxide powder, and a carbon powder according to the user.

Meanwhile, the foregoing sub raw material mixing step (S20) is performed by sequentially performing a sub raw material preparation step (S21) of preparing a sub raw material by pulverizing the sub raw material at the particle size each differentiated within a range of 30 nm to 10 μm, and then dividing the sub raw material at each particle size, and a sub raw material introduction step (S22) of each introducing the sub raw material prepared at each particle size into each of the main raw materials having the same particle size.

In other words, a sub raw material pulverized to a particle size of 30 nm is introduced into and mixed with a main raw material having a particle size of 30 nm, and a sub raw material pulverized to a particle size of 20 μm is introduced into and mixed with a main raw material having a particle size of 20 μm.

The following table is a table comparing and analyzing the mutual implantation time and implantation power as a zirconia block composed of only the main raw material (Example 1) and a zirconia block mixed with the main raw material and the sub raw material (Example 2) are each introduced into the coloring solution.

Meanwhile, as the main raw material used in Example 1, a raw material in which the main raw material and the sub raw material were mixed at a ratio of 85 to 90 wt % and 10 to 15 wt % was used.

TABLE 2

Comparison table of implantation powers of coloring solution by mixing of sub raw material

| Classification | Natural tooth | Example 1 | Example 2 |
|---|---|---|---|
| A1 | #FFCBCB | 99.5% | 99.8% |
| A2 | #FFDDDD | 99% | 99.5% |
| A3 | #FFE6DC | 98.5% | 99.2% |
| A4 | #FFDCDC | 99.5% | 99.7% |
| A5 | #FFEFEF | 99% | 99.1% |
| A6 | #FFFFFF | 100% | 100% |

<Comparison Table of Implantation Powers of Coloring Solution by Mixing of Sub Raw Material>

As described above, it could be confirmed that the zirconia block in which the sub raw material was mixed usually had colorization improved by 0.1 to 1% as compared to the zirconia block composed of only the main raw material.

The foregoing raw material pressurization step (S30) is a step in which the main raw material mixed with the sub raw material is injected into a mold for compression molding in an order of descending particle size or ascending particle size, and then is compression molded in the form of a block, and in addition, in order to mold a mixed raw material in which the main raw material and the sub raw material are mixed, it is the most preferred method to use a mold for compression molding, but the method is not limited to the mold for compression molding.

Meanwhile, in the foregoing raw material pressurization step (S30), the main raw material and the sub raw material injected into the mold for compression molding are molded in the form of a block by pressurization of the mold for compression molding, and in this case, the mold for compression molding molds the rave material by a method of gradually increasing pressure by performing a first pressurization under a force of 500 to 600 kg/km², again performing a secondary pressurization under a force of 700 to 800 kg/km², and finally performing a tertiary pressurization under a force of 800 to 1,000 kg/km².

As described above, the reason why the molding is performed in parallel from the low pressure to the high pressure is to maintain the separation space formed between the powders to the maximum in order to improve the color permeation force of the zirconia block.

The foregoing raw material implantation step (S40) is a step of inducing a coloring solution to permeate into the zirconia block by putting the molded zirconia block into a tank containing the coloring solution and then applying heat to the tank.

The raw material implantation step (S40) was expressed as putting the zirconia block into a tank containing a coloring solution, and then applying heat thereto, but more preferably, when the color solution contained in the tank is first heated at 50 to 100° C., and then the zirconia block is put into the tank, the generation of cracks caused by the difference in temperature is prevented by improving the strength in the block.

Further, in the foregoing raw material implantation step (S40), it is the most perfect condition for implanting a color to the zirconia block to immerse the zirconia block into a coloring solution at 35 to 50° C. for 10 to 30 minutes.

The foregoing heat treatment finishing step (S50) is a step of drying the zirconia block permeated with the coloring solution, and then drying the zirconia block at room temperature, and more specifically, the color-implanted zirconia block is brought out of the tank, placed onto a mesh net, and then primarily dried in a drying furnace in which hot wind at 5 to 20° C. is provided from all sides for 20 to 30 minutes, and again secondarily dried in a drying furnace in which hot wind at 10 to 25° C. is provided from all sides for 10 to 20 minutes. The thus dried zirconia block is put into a sintering furnace in order to remove metal chlorides in the block, and then calcined.

The zirconia block for a dental prosthesis finished by sequentially performing the main raw material separation step (S10); the sub raw material mixing step (S20); the raw material pressurization step (S30); the raw material implantation step (S40); and the heat treatment finishing step (S50) is quite different from a zirconia block obtained by the existing method of manually painting each different color to each layer of the zirconia block by using a coloring liquid method in order to express a color gradient equivalent to that of a natural tooth, such that it is possible to produce a zirconia block for a dental prosthesis in which the quality of the color gradient improved more easily; more rapidly, and constantly by differentiating the degree of color sense implanted at each part as the water absorption rate is differently constituted at each layer of the zirconia block, and thus the amount of coloring solution permeating into the corresponding layer is changed, and the sub raw material controlling the water absorption rate is prepared by mixing a powder selected from the group consisting of a silica powder, a hydroxyapatite powder, an yttrium oxide powder, a carbon powder, and a mixture thereof with the main raw material, thereby increasing the limitation of the color range of the zirconia block capable of being implanted at each layer.

Finally, since the zirconia block is directly produced in the aforementioned manner by medical equipment production companies, a patient can be immediately treated with a consistently high-quality crown for an implant having a color gradient without separate coloring liquid work in a dental clinic or a dental laboratory.

Although the present invention described above has been described with reference to an example illustrated in the drawings, this is illustrative only, and a person with ordinary skill in the art will understand that various modifications and other equivalent exemplary embodiments can be made therefrom. Therefore, the true technical protection scope of the present invention must be interpreted by the accompanying claims, and it should be interpreted that all technical sprits within a scope equivalent thereto are included in the right scope of the present invention.

INDUSTRIAL APPLICABILITY

The present invention relates to a method for manufacturing a zirconia block for a dental prosthesis with improved aesthetic properties, and more particularly, to a method for manufacturing a zirconia block for a dental prosthesis having a layered color gradient by water absorption rate, in which the permeation degree of a coloring solution is controlled by setting a different particle size of powder for each layer of the zirconia block on the basis of the property, that the amount of water absorption per hour is differentiated according to the particle size of powder, and as a result, the zirconia block is constituted so as to realize an esthetically excellent resultant product with the same color as natural teeth without carrying out the existing coloring liquid process for zirconia.

The invention claimed is:

1. A method for manufacturing a zirconia block for a dental prosthesis having a layered color gradient by a water absorption rate; the method comprising:
　1) a main raw material separation step of preparing a main raw material by pulverizing zirconia to different particle sizes and dividing the zirconia at each particle size;
　2) a sub raw material mixing step of introducing and mixing a sub raw material whose water absorption rate is controlled at each main raw material having a different particle size;
　3) a raw material pressurization step of injecting the main raw material mixed with the sub raw material into a mold for compression molding in an order of particle size; and then compression molding the main raw material in the form of a block;
　4) a raw material implantation step of inducing a coloring solution to permeate into the zirconia block by putting the zirconia block molded in step 3) into a tank containing the coloring solution and then applying heat to the tank; and
　5) a heat treatment finishing step of drying the zirconia block into which the coloring solution in step 4) penetrates, and then drying the zirconia block at room temperature.

2. The method of claim 1, wherein 1) the main raw material separation step pulverizes the zirconia into a particle size each differentiated within a range of 30 nm to 10 μm.

3. The method of claim 1, wherein 2) the sub raw material mixing step further comprises:
　2-1) a sub raw material preparation step of preparing the sub raw material by pulverizing the sub raw material into a particle size each differentiated within a range of 30 nm to 10 μm and dividing the sub raw material at each particle size; and
　2-2) a sub raw material introduction step of each introducing the sub raw material prepared at each particle size into each of the main raw materials having the same particle size.

4. The method of claim 1, wherein 3) the raw material pressurization step comprises:
　3-1) a step of firstly pressurizing the raw material at 500 to 600 kg/km$^2$;
　3-2) a step of secondly pressurizing the raw material at 700 to 800 kg/km$^2$; and
　3-3) a step of thirdly pressurizing the raw material at 800 to 1000 kg/km$^2$.

5. The method of claim 1, wherein 4) the raw material implantation step comprises:
　4-1) a step of heating a coloring solution to 50 to 100° C.; and
　4-2) a step of putting a zirconia block into the heated coloring solution.

6. The method of claim 1, wherein 5) the heat treatment finishing step comprises:
　5-1) a step of firstly drying the zirconia block in a drying furnace in which hot wind at 5 to 20° C. is provided from all sides for 20 to 30 minutes;
　5-2) a step of secondly drying the zirconia block in a drying furnace in which hot wind at 10 to 25° C. is provided from all sides for 10 to 20 minutes; and
　5-3) a step of putting the dried zirconia block into a sintering furnace and calcining the zirconia block.

7. The method of claim 1, wherein the sub raw material is selected from the group consisting of a silica powder, a hydroxyapatite powder, an yttrium oxide powder, a carbon powder, and a mixture thereof.

* * * * *